(12) United States Patent
Yu et al.

(10) Patent No.: US 8,686,039 B2
(45) Date of Patent: Apr. 1, 2014

(54) AQUEOUS NANOEMULSION COMPOSITION CONTAINING CONJUGATED LINOLEIC ACID

(75) Inventors: Hyo Gyoung Yu, Goyang (KR); Hong Geun Ji, Bucheon (KR); Hye Kyeong Woo, Seoul (KR); Soo Dong Kim, Youngdeungpo-gu (KR)

(73) Assignees: Hwail Pharmaceutical Co., Ltd., Gangnam-Su, Seoul (KR); Yu, Hyo Gyoung, Goyang, Gyeonggi-Do (KR)

( * ) Notice: Subject to any disclaimer, the term of this patent is extended or adjusted under 35 U.S.C. 154(b) by 86 days.

(21) Appl. No.: 13/142,626

(22) PCT Filed: Feb. 19, 2010

(86) PCT No.: PCT/KR2010/001029
§ 371 (c)(1),
(2), (4) Date: Jun. 29, 2011

(87) PCT Pub. No.: WO2010/095877
PCT Pub. Date: Aug. 26, 2010

(65) Prior Publication Data
US 2012/0053241 A1    Mar. 1, 2012

(30) Foreign Application Priority Data
Feb. 20, 2009 (KR) .................. 10-2009-0014347

(51) Int. Cl.
A01N 37/00 (2006.01)
A61K 31/20 (2006.01)
A23L 1/236 (2006.01)
A23L 2/00 (2006.01)
A23L 2/38 (2006.01)
A21D 2/16 (2006.01)

(52) U.S. Cl.
USPC ............ 514/560; 426/548; 426/590; 426/654

(58) Field of Classification Search
USPC .......................... 514/560; 426/548, 590, 654
See application file for complete search history.

(56) References Cited

U.S. PATENT DOCUMENTS

| 2006/0057187 A1* | 3/2006 | Eskuchen et al. ............. 424/439 |
| 2008/0199589 A1* | 8/2008 | Patist et al. .................... 426/602 |
| 2009/0297665 A1* | 12/2009 | Bromley ........................ 426/72 |

FOREIGN PATENT DOCUMENTS

| JP | 2002265374 | 9/2002 |
| JP | 2007282574 | 11/2007 |
| WO | 9718320 | 5/1997 |
| WO | WO 2008/065451 | * 6/2008 |

OTHER PUBLICATIONS

JP 2007-282574, (English translation of the document).*
Kentish et al. (Innovative Food Sci and Emerging Technologies, 9, 2008, 170-175).*
International Search Report mailed Sep. 29, 2010 for PCT/KR2010/001029.

* cited by examiner

*Primary Examiner* — Sreeni Padmanabhan
*Assistant Examiner* — Uma Ramachandran
(74) *Attorney, Agent, or Firm* — Clark G. Sullivan; Troutman Sanders LLP

(57) ABSTRACT

The present invention relates to an aqueous nanoemulsion composition comprising conjugated linoleic acid. More particularly, the present invention relates to an aqueous nanoemulsion composition comprising 5 to 50 wt % of conjugated linoleic acid, 0.01 to 5 wt % of lecithin, 0.01 to 5 wt % of ethanol as a dissolution aid, 1 to 15 wt % of coemulsifier, 10 to 40 wt % of glycerine and the balance of water.

4 Claims, 6 Drawing Sheets w/ ethanol    w/o ethanol w/ ethanol w/o ethanol

AQUEOUS NANOEMULSION COMPOSITION CONTAINING CONJUGATED LINOLEIC ACID

TECHNICAL FIELD

The present invention relates to an aqueous nanoemulsion composition comprising conjugated linoleic acid. More particularly, the present invention relates to an aqueous nanoemulsion composition comprising 5 to 50 wt % of conjugated linoleic acid, 0.01 to 5 wt % of lecithin, 0.01 to 5 wt % of ethanol as a dissolution aid, 1 to 15 wt % of coemulsifier, 10 to 40 wt % of glycerine and the balance of water.

BACKGROUND ART

Lipids are classified into various categories, among which the most important is fatty acid. Fatty acids are divided into the saturated fatty acid group and the unsaturated fatty acid group according to the presence of a double bond. Animal fats such as butter or beef tallow mainly consist of saturated fatty acids and are characterized by existing in solid state at room temperature. Vegetable fats and fish oil mainly consist of unsaturated fatty acids. Fatty acid has a structure in which carbon atoms are linked as a long chain. In the nomenclature of unsaturated fatty acid, it is designated as delta ($\Delta$) in case of counting the carbon atom at which the double bond appears firstly from the carboxyl terminal and is designated as omega ($\omega$) in case of counting the carbon atom at which the double bond appears firstly from the methyl terminal. In case of omega nomenclature, it is also designated as "n-." For example, omega-3 fatty acid refers to a fatty acid wherein the first double bond is located on the $3^{rd}$ carbon-carbon bond from the methyl ($CH_3$—) group. In the same manner, omega-6 fatty acid refers to a fatty acid wherein the first double bond is located on the $6^{th}$ carbon-carbon bond from the methyl group. In terms of the content of n-3 and n-6 fatty acids in food usually used as a lipid source, most vegetable foods are richer in n-3 and n-6 fatty acids than animal foods. Among edible oils and fats, n-6 fatty acid-enriched examples are corn oil, cottonseed oil, etc.; n-3 fatty acid-enriched examples are linseed oil and fish oils such as salmon oil; and both n-6 fatty acid and n-3 fatty acid-enriched examples in balance are soybean oil and walnut oil. Among n-6 fatty acids and n-3 fatty acids, linoleic acid (LA), $\alpha$-linolenic acid (LNA) and arachidonic acid (AA) are classified into an essential fatty acid (EFA) group that humans should essentially ingest, and so they are nutritionally important. Specifically, LA and LNA are elongated or desaturated via biosynthesis procedures after digestion to fatty acids having 20 to 22 carbon atoms chain with 4 to 6 carbon-carbon double bonds. Representative examples of such fatty acids are docosahexaenoic acid (DHA) and eicosapentaenoic acid (EPA). Examples of omega-3 fatty acids are alpha linolenic acid, DHA, EPA, etc. Such omega-3 fatty acids are essential in cell generation and regeneration, and are associated with health of the cardiovascular system—e.g., blood pressure, blood coagulation, lowering of cholesterol level, etc. They are also helpful for arthritis, rheumatism, development and regulation of brain and nerve function, health of skin and hair, and optical health. Examples of omega-6 fatty acids are alpha linoleic acid, arachidonic acid, gamma linoleic acid, etc. The functions of omega-6 fatty acids are to prevent arteriosclerosis, heart disease, premenstrual syndrome (PMS), hypercholesterolemia and hypertension, to alleviate pain and inflammation, and to improve the secretion of sex hormones such as estrogen, testosterone, etc. Omega-6 fatty acids are also helpful for hepatic cirrhosis and have efficacy in the prevention of aging, maintenance of skin health, prevention of obesity and diabetes complications, and alleviation of rheumatic arthritis. An example of omega-9 fatty acids is oleic acid.

Some important functions of lipids, when ingested from food or synthesized in the human body, are as follows: First, major constitutional components of cell membranes (phospholipids, glycolipids and steroids); second, storable high-energy source; third, protective membrane and insulating material for subcutaneous tissue or major organs; fourth, facilitation of excitation conduction in myelinated neurons (non-polar lipids); fifth, conversion to various biological active materials (lipid-soluble vitamins, essential fatty acids, steroid hormones, bile acid, prostaglandin, leukotriene, etc.). As can be seen above, lipids play very important and various roles in the human body. Specifically, polyunsaturated fatty acids (PUFA) are not only constitutional components of phospholipids but are converted into prostaglandins (PG), leukotrienes (LT) and important thromboxanes (TX) via in vivo metabolism and then play important roles in maintaining and regulating various physiological phenomena.

Conjugated linoleic acid (CLA) is a kind of fatty acid which is formed by the modification of the chemical structure of linoleic acid. As its name indicates, CLA has conjugated double bonds. CLA has various physiological activities. Up to now, it has been known as having anticancer activity, antioxidant activity, antiarteriosclerotic activity, antibacterial activity as well as prevention and treating effect on various adult diseases. In addition, it has been known that CLA directly acts on adipocytes in the body to prevent them from absorbing fat, and it aids in reduction of body fat—specifically abdominal fat—by reducing adipocytes by increasing apoptosis of adipocytes by means of increasing degradation and metabolic rate of adipocytes, and facilitating the use of fat as energy for strengthening muscle. As a result, CLA has attracted wide attention as a body-slimming material.

As society continues to advance and develop, the desire for a slim figure has been increasing in proportion to improvement of the standard of living. To satisfy such a desire, attempts have been made to develop a body-slimming material, specifically one from natural products. However, many functional materials used in food, beverages, cosmetics and in the pharmaceutical field originate from natural products, and thus most functional materials are unstable to exterior environmental factors such as light, heat, oxygen, etc. and are insoluble in water, conventional organic solvents and oil. As a result, in spite of their remarkable efficacy and/or effect, the use of functional materials is limited. Examples of such materials are too many to enumerate. At present, functional materials are used after being stabilized by methods of emulsification or encapsulation in solution by the use of surfactant or emulsifier. However, such methods cannot sufficiently physically or chemically stabilize functional materials since micelles are coagulated or functional materials are self-degraded by diffusion in solution. Thus, there is a limited practical use in industry. To resolve such problems, many studies are being carried out in each field, but a satisfactory solution has not yet been achieved.

DISCLOSURE

The object of the present invention is to provide an aqueous nanoemulsion composition containing conjugated linoleic acid as an effective ingredient, with remarkable storage stability, pH stability and transparency.

To accomplish the above object, the present invention provides an aqueous nanoemulsion composition comprising 5 to 50 wt % of conjugated linoleic acid, 0.01 to 5 wt % of lecithin, 0.01 to 5 wt % of ethanol as a dissolution aid, 1 to 15 wt % of coemulsifier, 10 to 40 wt % of glycerine and the balance of water.

MODE FOR INVENTION

Figure 1:
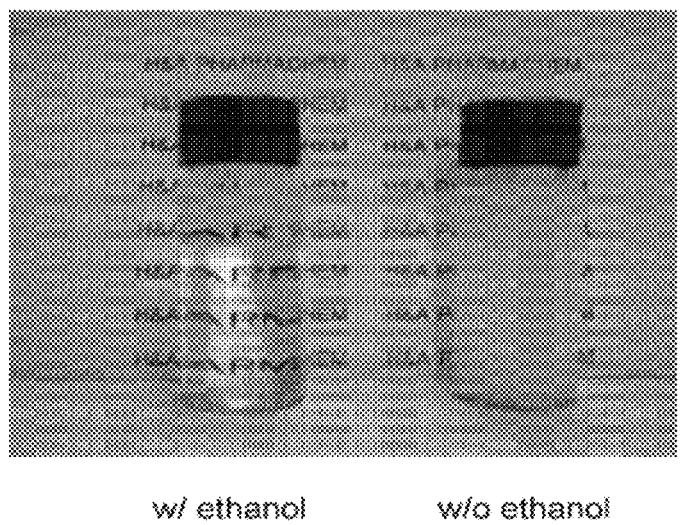
FIG. 1 is a photograph to compare the transparency of nanoemulsion comprising ethanol with that of nanoemulsion not comprising ethanol.

The present invention is described in detail hereinafter.

The present aqueous nanoemulsion composition comprises conjugated linoleic acid as an active ingredient. There is no limit on the kind of conjugated linoleic acid, and any commercially available conjugated linoleic acid may be used. Such conjugated linoleic acid includes, for example, Tonalin™ CLA (Cognis, Germany), Clarinol™ CLA (Lipid Nutrition B.V., Netherlands), CLA (HK Biotech, Korea), etc.

The present aqueous nanoemulsion composition comprises conjugated linoleic acid in an amount of 5 to 50 wt %, preferably 10 to 45 wt %, and more preferably 15 to 40 wt %. In the present invention, if the amount of conjugated linoleic acid is less than 5 wt %, the biological activity effect of conjugated linoleic acid may be weak, and if the amount of conjugated linoleic acid is more than 50 wt %, conjugated linoleic acid may be poorly dissolved or may be precipitated when exposed to air for a long time.

The present aqueous nanoemulsion composition comprises lecithin as an emulsifier. In the present invention, lecithin refers to a mixture of various phospholipids, and the composition of phospholipids may vary according to origin. In the present invention, lecithin may be derived from various origins such as egg yolk, soybean oil, sunflower seed oil, etc., and there is no limit according to the kind of origin. When the present aqueous nanoemulsion composition is orally administered as beverage or functional food, conjugated linoleic acid can be rapidly penetrated by using lecithin, which is an amphiphilic emulsifier. The present aqueous nanoemulsion composition comprises lecithin in an amount of 0.01 to 5 wt %, preferably 0.1 to 4 wt %. In the present invention, if the amount of lecithin is less than 0.01 wt %, the emulsifying effect provided by lecithin may be weak and emulsification stability may be lowered, and if the amount of lecithin is more than 5 wt %, viscosity of composition may be too high.

The present aqueous nanoemulsion composition comprises ethanol as a dissolution aid to help dissolution of conjugated linoleic acid. The present aqueous nanoemulsion composition comprises ethanol in an amount of 0.01 to 5 wt %, preferably 0.1 to 4 wt %. In the present invention, if the amount of ethanol is less than 0.01 wt %, the effect on helping dissolution of conjugated linoleic acid may be weak, and if the amount of ethanol is more than 5 wt %, emulsification stability may be lowered.

The present aqueous nanoemulsion composition comprises a coemulsifier to emulsify conjugated linoleic acid more stably. In the present invention, the examples of coemulsifiers preferably include Polysorbate 20 (polyoxyethylene (20) sorbitan monolaurate, trademark Tween 20); Polysorbate 80 (polyoxyethylene (20) sorbitan monooleate, trademark Tween 80); anionic amino acid-based emulsifier, sugar esters, cholesterol, sodium lauryl sulfate, sodium stearoyl lactylate and glycerine ester. In the present invention, the examples of said anionic amino acid-based emulsifier includes, but are not limited to, TEA (triethanolamine)-cocoyl glutamate, sodium glutamate, sodium cocoyl glutamate, magnesium cocoyl glutamate and sodium lauroyl glutamate. The present aqueous nanoemulsion composition comprises coemulsifier in an amount of 1 to 15 wt %, preferably 3 to 13 wt %, and more preferably 5 to 12 wt %. In the present invention, if the amount of coemulsifier is less than 1 wt %, emulsification stability may be lowered, and if the amount of ethanol is more than 5 wt %, viscosity of composition may be too high.

The present aqueous nanoemulsion composition comprises glycerine to prevent precipitation of conjugated linoleic acid and dissolve conjugated linoleic acid with a relatively small amount of emulsifier. The present aqueous nanoemulsion composition comprises glycerine in an amount of 10 to 40 wt %, preferably 12 to 38 wt %, and more preferably 15 to 35 wt %. In the present invention, if the amount of glycerine is less than 10 wt %, storage stability of the present aqueous nanoemulsion composition may be lowered, and if the amount of ethanol is more than 40 wt %, taste, texture or flavor may be lowered when the present composition is used in beverage or food.

The present aqueous nanoemulsion composition comprising conjugated linoleic acid preferably has viscosity of 1 to 100 cP (centipoise). The present aqueous nanoemulsion composition comprising conjugated linoleic acid has excellent storage stability so that precipitation or phase separation does not occur when it is stored for a long time at room temperature (25° C.) as well as high temperature (45° C.). In addition, because the present aqueous nanoemulsion composition comprising conjugated linoleic acid is stable in a wide range of pH, it can be used with various formulations. The present aqueous nanoemulsion composition comprising conjugated linoleic acid can be applied to beverages, food, cosmetics, functional food or medicines according to the desired purpose. To such applications, the present aqueous nanoemulsion composition comprising conjugated linoleic acid may further comprise various additives such as a viscosity agent, sweetener, excipient, flavor, etc.

The present aqueous nanoemulsion composition comprising conjugated linoleic acid has excellent storage stability, pH stability and transparency, and can efficiently penetrate conjugated linoleic acid.

Hereinafter, the present invention is explained in more detail with the following examples. However, it must be understood that the protection scope of the present invention is not limited to the examples.

EXAMPLE 1

An aqueous nanoemulsion composition was prepared by the following method with the composition of Table 1. Conjugated linoleic acid and lecithin were dissolved in sugar ester and ethanol. Then, water and glycerine were added thereto and sufficiently agitated. The resulting mixture was continuously passed five (5) times through a high-pressure microfluidizer at 1,000 bar, followed by sterile filtration of the mixture to obtain a nanoemulsion composition. This composition was dispensed and packaged.

TABLE 1

| Ingredient | Content (wt %) |
| --- | --- |
| Conjugated linoleic acid | 30 |
| Ethanol | 2.5 |
| Lecithin | 2.5 |
| Sugar ester | 8 |
| Glycerine | 20 |
| Water | 37 |
| Total amount | 100 |

EXAMPLE 2

An aqueous nanoemulsion composition was prepared by the same method as described in Example 1 except that the constitutional composition of the following Table 2 was used.

TABLE 2

| Ingredient | Content (wt %) |
| --- | --- |
| Conjugated linoleic acid | 30 |
| Ethanol | 2.5 |
| Lecithin | 2.5 |
| Cholesterol | 8 |
| Glycerine | 30 |
| Water | 27 |
| Total amount | 100 |

EXAMPLE 3

An aqueous nanoemulsion composition was prepared by the same method as described in Example 1 except that the constitutional composition of the following Table 3 was used.

TABLE 3

| Ingredient | Content (wt %) |
| --- | --- |
| Conjugated linoleic acid | 30 |
| Ethanol | 2.5 |
| Lecithin | 2.5 |
| Cholesterol | 5 |
| Polysorbate 20 | 4 |
| Glycerine | 25 |
| Water | 31 |
| Total amount | 100 |

EXAMPLE 4

An aqueous nanoemulsion composition was prepared by the same method as described in Example 1 except that the constitutional composition of the following Table 4 was used.

TABLE 4

| Ingredient | Content (wt %) |
| --- | --- |
| Conjugated linoleic acid | 30 |
| Ethanol | 2.5 |
| Lecithin | 2.5 |
| Sugar ester | 5 |
| Polysorbate 80 | 4 |
| Glycerine | 25 |
| Water | 31 |
| Total amount | 100 |

EXAMPLE 5

An aqueous nanoemulsion composition was prepared by the same method as described in Example 1 except that the constitutional composition of the following Table 5 was used.

TABLE 5

| Ingredient | Content (wt %) |
| --- | --- |
| Conjugated linoleic acid | 30 |
| Ethanol | 2.5 |
| Lecithin | 2.5 |
| Glycerine ester | 8 |
| Glycerine | 20 |
| Water | 37 |
| Total amount | 100 |

EXAMPLE 6

An aqueous nanoemulsion composition was prepared by the same method as described in Example 1 except that the constitutional composition of the following Table 6 was used.

TABLE 6

| Ingredient | Content (wt %) |
| --- | --- |
| Conjugated linoleic acid | 35 |
| Ethanol | 2.5 |
| Lecithin | 2 |
| Glycerine ester | 5 |
| Polysorbate 80 | 5 |
| Glycerine | 28 |
| Water | 22.5 |
| Total amount | 100 |

EXAMPLE 7

An aqueous nanoemulsion composition was prepared by the same method as described in Example 1 except that the constitutional composition of the following Table 7 was used.

TABLE 7

| Ingredient | Content (wt %) |
| --- | --- |
| Conjugated linoleic acid | 35 |
| Ethanol | 2.5 |
| Lecithin | 2 |
| Sugar ester | 5 |
| Sodium lauryl sulfate | 5 |
| Glycerine | 28 |
| Water | 22.5 |
| Total amount | 100 |

EXAMPLE 8

An aqueous nanoemulsion composition was prepared by the same method as described in Example 1 except that the constitutional composition of the following Table 8 was used.

TABLE 8

| Ingredient | Content (wt %) |
| --- | --- |
| Conjugated linoleic acid | 35 |
| Ethanol | 2.5 |
| Lecithin | 2 |
| Glycerine ester | 5 |
| Sodium lauryl sulfate | 5 |
| Glycerine | 28 |
| Water | 22.5 |
| Total amount | 100 |

EXAMPLE 9

An aqueous nanoemulsion composition was prepared by the same method as described in Example 1 except that the constitutional composition of the following Table 9 was used.

TABLE 9

| Ingredient | Content (wt %) |
| --- | --- |
| Conjugated linoleic acid | 35 |
| Ethanol | 2.5 |
| Lecithin | 2 |
| Sugar ester | 5 |
| Sodium glutamate | 5 |
| Glycerine | 28 |
| Water | 22.5 |
| Total amount | 100 |

EXAMPLE 10

An aqueous nanoemulsion composition was prepared by the same method as described in Example 1 except that the constitutional composition of the following Table 10 was used.

TABLE 10

| Ingredient | Content (wt %) |
| --- | --- |
| Conjugated linoleic acid | 35 |
| Ethanol | 2.5 |
| Lecithin | 2 |
| Glycerine ester | 5 |
| Sodium glutamate | 5 |
| Glycerine | 28 |
| Water | 22.5 |
| Total amount | 100 |

EXPERIMENTAL EXAMPLE 1

Appearance of the compositions prepared in Examples 1 to 10 was observed with the naked eye about phase separation and precipitation. Stability was measured by the content change of conjugated linoleic acid after storage in 25° C. and 45° C. thermostatic baths.

Measurement of Content of Conjugated Linoleic Acid 20 to 25 mg of sample was added to 2 mL of 0.5N NaOH methanol solution and shaken, and then heated in 80° C. heating bath for 10 minutes and cooled with cold water. 2 mL of $BH_3$ was added thereto, then heated in 80° C. heating bath for 8 to 10 minutes and cooled with cold water. 3 mL of internal standard solution (a solution of 500 mg of undecanoic acid dissolved in 100 mL of n-hexane) was added thereto, then heated in 80° C. heating bath for 3 minutes and cooled with cold water. 5 mL of saturated NaCl solution was added thereto for phase separation, and then the upper layer was taken and 0.5 g of anhydrous sodium sulfate was added thereto to remove moisture. 1 μl of the prepared test solution was analyzed by gas chromatography (column: DB-Wax; injector temperature: 270° C.; detector temperature: 290° C.; column temperature: 190-240° C., temperature was raised by 2° C. per minute).

1) Phase Separation, Precipitation and Stability

TABLE 11

| | Appearance | | Stability (content of CLA, %) | | | | | |
| --- | --- | --- | --- | --- | --- | --- | --- | --- |
| | Phase | | Room temperature (25□) | | | High temperature (45□) | | |
| | separation | Precipitation | Initial | 1 year | 2 years | Initial | 1 year | 2 years |
| Example 1 | Good | Good | 100 | 100 | 98.4 | 100 | 100 | 98.1 |
| Example 2 | Good | Good | 100 | 100 | 99.1 | 100 | 100 | 98.9 |
| Example 3 | Good | Good | 100 | 100 | 98.1 | 100 | 100 | 97.9 |
| Example 4 | Good | Good | 100 | 100 | 99.5 | 100 | 100 | 99.0 |
| Example 5 | Good | Good | 100 | 100 | 98.9 | 100 | 100 | 98.1 |
| Example 6 | Good | Good | 100 | 100 | 97.9 | 100 | 100 | 98.1 |
| Example 7 | Good | Good | 100 | 100 | 99.1 | 100 | 100 | 99.0 |
| Example 8 | Good | Good | 100 | 100 | 99.3 | 100 | 100 | 99.3 |

TABLE 11-continued

| | Appearance | | Stability (content of CLA, %) | | | | | |
|---|---|---|---|---|---|---|---|---|
| | Phase | | Room temperature (25□) | | | High temperature (45□) | | |
| | separation | Precipitation | Initial | 1 year | 2 years | Initial | 1 year | 2 years |
| Example 9 | Good | Good | 100 | 100 | 98.9 | 100 | 100 | 98.9 |
| Example 10 | Good | Good | 100 | 100 | 99.4 | 100 | 100 | 99.3 |

2) Color change at room temperature (25° C.) and high temperature (45° C.) was observed for 2 years. No color change was observed.

3) pH Stability pH stability in pH 2, 5, 7 and 10 at room temperature (25° C.) was observed with the naked eye about phase separation and precipitation. The result is represented in the following Table 12.

TABLE 12

| | pH | | | |
|---|---|---|---|---|
| | 2 | 5 | 7 | 10 |
| Example 1 | Good | Good | Good | Good |
| Example 2 | Good | Good | Good | Good |
| Example 3 | Good | Good | Good | Good |
| Example 4 | Good | Good | Good | Good |
| Example 5 | Good | Good | Good | Good |
| Example 6 | Good | Good | Good | Good |
| Example 7 | Good | Good | Good | Good |
| Example 8 | Good | Good | Good | Good |
| Example 9 | Good | Good | Good | Good |
| Example 10 | Good | Good | Good | Good |

From the above result, it can be known that the present aqueous nanoemulsion composition has excellent storage stability, transparency without discoloring and stability in a wide range of pH.

EXPERIMENTAL EXAMPLE 2

Figure 2:
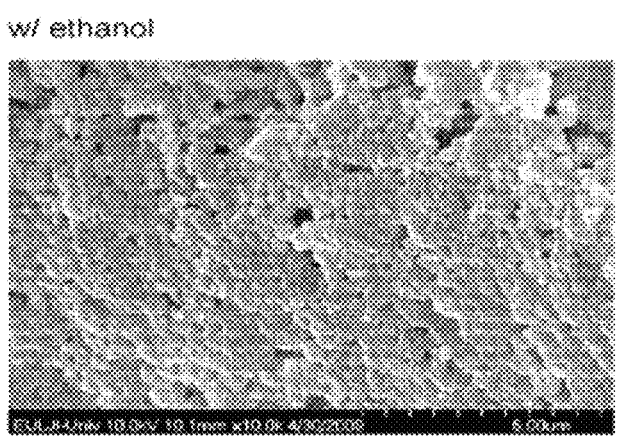
FIG. 2 is a scanning electron microscope photograph of nanoemulsion comprising ethanol and nanoemulsion not comprising ethanol (15,000 times magnification).
Figure 2:
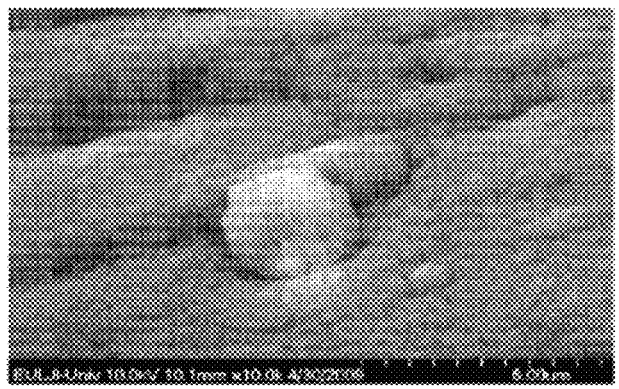

Nanoemulsion compositions were prepared as represented in Table 13 to compare nanoemulsion comprising ethanol as a dissolution aid with nanoemulsion not comprising ethanol. The particle size, transparency, viscosity and storage stability at 45° C. were measured, and the results are represented in the following Table 14. The particle size distribution was measured by using a Photal ELS-Z. In addition, for nanoemulsion comprising ethanol and nanoemulsion not comprising ethanol, a scanning electron microscope (JEOL, Japan) photograph was taken and the result is represented in FIG. 2.

TABLE 13

| Ingredient | With ethanol | Without ethanol |
|---|---|---|
| Conjugated linoleic acid | 30 | 30 |
| Lecithin | 2.5 | 2.5 |
| Ethanol | 2.5 | 0 |
| Sugar ester | 8 | 8 |
| Glycerine | 20 | 20 |
| Water | 37 | 39.5 |
| Total amount | 100 | 100 |

(Unit: wt %)

TABLE 14

| | With ethanol | Without ethanol |
|---|---|---|
| Particle size (nm) | 30.9 | 220.8 |
| Transparency | Very transparent | opaque |
| Viscosity (cP) | 50 | 1,000 |
| 45° C. stability (1 month) | No phase separation | Phase separated |

As can be seen in the above Table 14, when ethanol was added as a dissolution aid, an emulsion having 30.9 nm of average particle size was formed, whereas when ethanol was not added, the average particle size of emulsion was 220.8 nm. Thus, it can be known that stable nanoemulsion can be obtained when ethanol was added. In addition, with respect to transparency, when ethanol was added, very transparent composition can be obtained, whereas when ethanol was not added, opaque composition was obtained. With respect to viscosity, there is a considerable difference in that viscosity of the composition comprising ethanol was 50 cP, whereas that of the composition which did not comprise ethanol is 1,000 cP. With respect to storage stability, when ethanol was added, phase separation was not observed after storage at 45° C. for one month, whereas when ethanol was not added, phase separation occurred. Thus, it can be known that the composition comprising ethanol is better in terms of storage stability. Furthermore, in comparing scanning electron microscope photographs, when ethanol was added, uniform nanoemulsion was formed, whereas when ethanol was not added, large emulsion particles coagulated each other.

EXPERIMENTAL EXAMPLE 3

To investigate the anti-obesity effects of the present aqueous nanoemulsion composition comprising conjugated linoleic acid, in vitro and in vivo experiments were conducted. DMSO (dimethyl sulfoxide, control), Orlistat (anti-obesity drug, positive-control), CLA and the present aqueous nanoemulsion composition comprising conjugated linoleic acid (hereinafter referred to as "N-CLA") were used as samples. N-CLA was prepared according to the method described in Example 1.

EXPERIMENTAL EXAMPLE 3-1

In Vitro Experiments (1) Cell Culture and Sample Treatment

3T3-L1 pre-adipocytes were cultured in Dulbecco's Modified Eagle's Medium (DMEM) containing 10% fetal bovine serum, 100 unit/mL penicillin and 10 μg/mL streptomycin at 37° C., 5% $CO_2$ incubator. When 70 to 80% of cells were confluent, cells were pre-differentiated with DMEM containing dexamethazone, pioglitazone, IBMX (3-isobutyl-1-methylxanthin), insulin and FBS which are differentiation inducers, and then were differentiated with DMEM containing insulin, pioglitazone and FBS. After differentiation, lipids were matured with growth medium containing 10% FBS and insulin. Samples were dissolved in DMSO and treated in 10 µg/mL of the final concentration.

(2) Cell Viability (MTT Assay)

Figure 3:
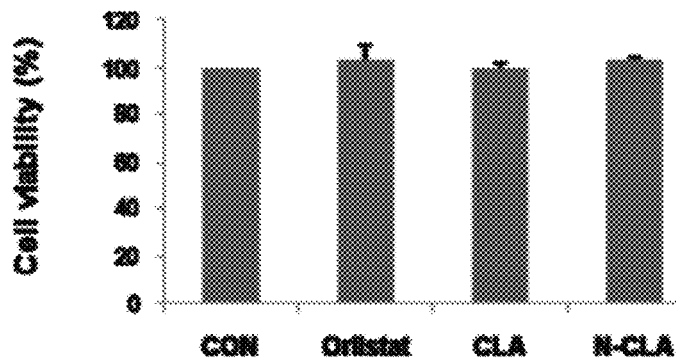
FIG. 3 is a graph representing the results of cell viability measured by using MTT assay (Control: DMSO, Orlistat: positive control, CLA: conjugated linoleic acid, N-CLA: nanoemulsion conjugated linoleic acid).

$1 \times 10^4$ pre-adipocytes were dispensed into each well of 96-well plate, and each sample was treated. Then cells were incubated at 37° C., 5% $CO_2$ incubator for 24 hours. After 24 hours, MTT (in phosphate buffered saline, final concentration was 0.4 µg/mL) was treated, and then cells were incubated for 4 hours. Formed formazan crystal was dissolved with DMSO:ethanol (1:1) and absorbance at 540 nm was measured by a microplate reader (SUNRISE, TECAN, Austria). Cell viability was determined by the ratio of absorbance value of sample treating group to absorbance value of control group, and the results are represented in FIG. 3. As can be seen in FIG. 3, cell viability of the Orlistat group, CLA group and N-CLA group is 103%, 100% and 103%, respectively. Thus, there is no statistically significant difference from that of the control group.

Figure 4:
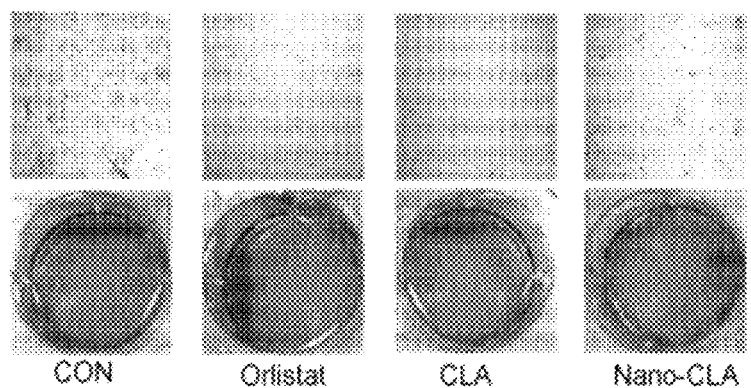
FIG. 4 is a photograph of a cell stained with Oil red O.
Figure 5:
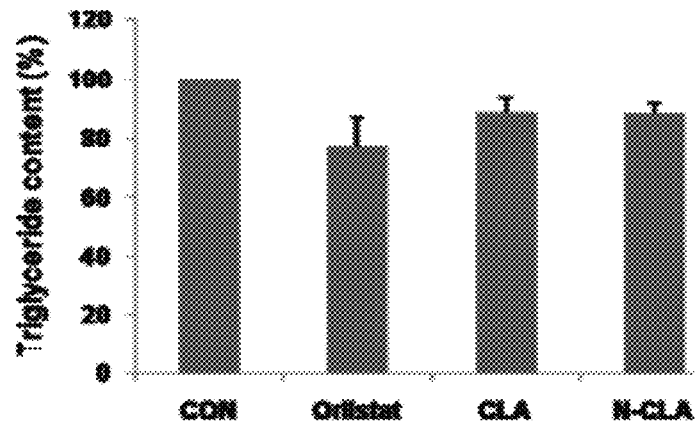
FIG. 5 is a graph representing the content of neutral lipid (Control: DMSO, Orlistat: positive control, CLA: conjugated linoleic acid, N-CLA: nanoemulsion conjugated linoleic acid).

(3) Lipolysis Effect $1 \times 10^5$ cells were dispensed into each well of 6-well plate and differentiated. On the $8^{th}$ day after differentiation, media were removed, and cells were washed twice with ice-cold PBS. Cells were fixed with 10% formalin at room temperature for 1 hour, stained with 0.2 Oil red O (in isoprophanol) for 30 minutes, and then washed with distilled water. Isopropanol was added thereto to dissolve oil droplets, and then the content of neutral lipids was measured as absorbance at 490 nm. The results are represented in FIGS. 4 and 5. The Orlistat group, CLA group and N-CLA group showed tendency of decreasing neutral lipids compared with the control group.

Figure 6:
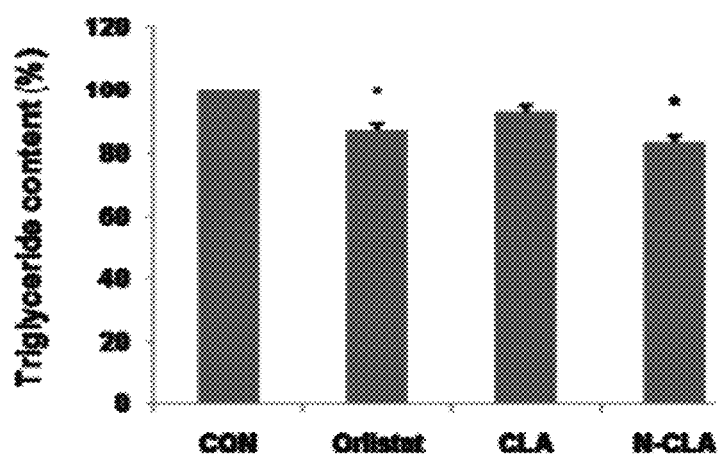
FIG. 6 is a graph representing the measurement result of the inhibitory effect on adipogenesis (Control: DMSO, Orlistat: positive control, CLA: conjugated linoleic acid, N-CLA: nanoemulsion conjugated linoleic acid; * $p<0.05$).

(4) Adipogenesis Inhibitory Effect $1 \times 10^5$ cells were dispensed into each well of 6-well plate. When 70% of cells were confluent, cells were treated with MDI medium (differentiation medium) and each sample at the same time, then incubated for 48 hours. On the $8^{th}$ day after differentiation, the content of neutral lipids was measured with Oil red O staining. The results are represented in FIG. 6. As can be seen in FIG. 6, the CLA group showed similar content of neutral lipids with the control group, whereas in the Orlistat group and N-CLA group, the content of neutral lipids was decreased with statistical significance in 12.5% and 16.3%, respectively, compared with the control group.

(5) Glycerol Quantification

Glycerol was quantified with an enzyme reaction method by using free glycerol reagent (Sigma, USA). 10 µl of medium, collected after treatment of cells with sample for 24 hours was added to 0.8 mL of Free glycerol reagent which was pre-warmed at 37° C., and then the reaction of the mixture was carried out in 37° C. water bath for 5 minutes. For quantification of glycerol, standard glycerol (25 µg/10 µl) was reacted in the same manner as above, and then absorbance at 540 nm was measured. The content of glycerol was calculated with the following formula.

$$\text{Glycerol content} = \frac{(A_{sample} - A_{blank})}{(A_{standard} - A_{blank})} \times \text{concentration of standard}$$

Figure 7:
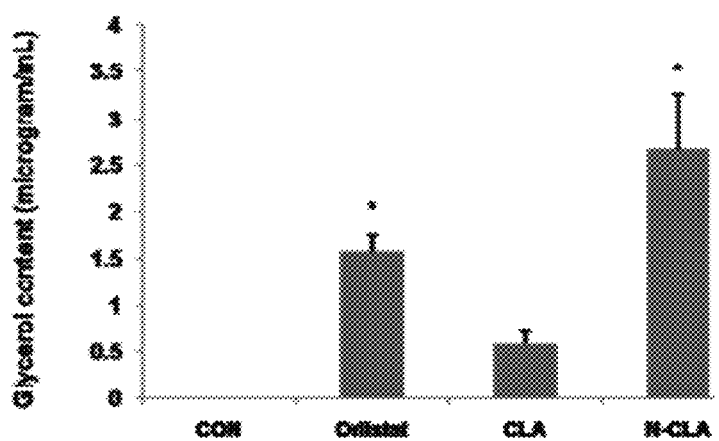
FIG. 7 is a graph representing the measurement result of the content of glycerol according to lipolysis (Control: DMSO, Orlistat: positive control, CLA: conjugated linoleic acid, N-CLA: nanoemulsion conjugated linoleic acid; * $p<0.05$).

The calculated result was represented in FIG. 7. As can be seen in FIG. 7, the CLA group showed a tendency of increasing the secretion of glycerol (lysis effect) compared with the control group, and the Orlistat group increased the secretion of glycerol in 1.57 µg/mL. Specifically, the content of glycerol of the N-CLA group was 2.67 µg/mL, and thus the secretion of glycerol in the N-CLA group was highest as compared with the other groups.

(6) Leptin Secretion

Figure 8:
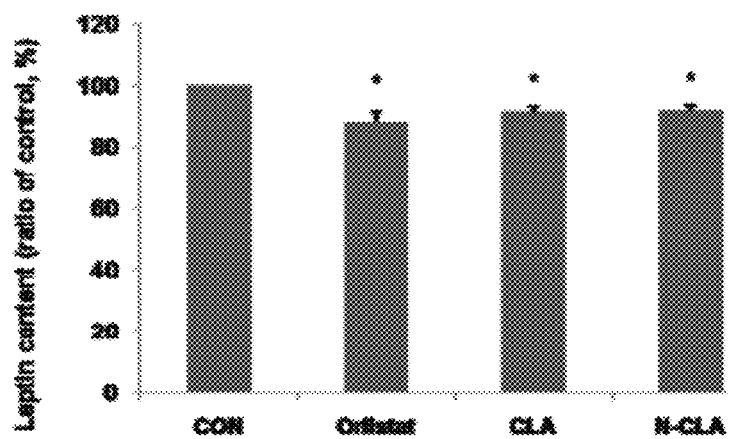
FIG. 8 is a graph representing the measurement result of the amount of leptin secreted from adipocyte (Control: DMSO, Orlistat: positive control, CLA: conjugated linoleic acid, N-CLA: nanoemulsion conjugated linoleic acid; * $p<0.05$).

An experiment was carried out to check whether the secretion amount of leptin, which is known as an appetite-related hormone, is regulated. The amount of leptin secreted from adipocytes was measured by enzyme-linked immunosorbent assay (ELISA) on media collected after treatment of adipocytes with sample. 100 µl of rabbit anti-mouse leptin IgG was aliquoted into an ELISA plate. The ELISA plate was incubated overnight at 4° C., washed with TPBS (PBS+0.05% Tween 20) three times, 100 µl of the collected medium was added thereto, and then it was incubated at room temperature for 1 hour. The ELISA plate was again washed with TPBS three times, secondary antibody was added thereto, incubated at room temperature for 1 hour, and then washed with TPBS three times. Color development was elicited by the use of alkaline phosphatase conjugated substrate kit, and then absorbance at 490 nm was measured by an ELISA reader (SUNRISE, TECAN, Austria). The results are represented in FIG. 8. As can be seen in FIG. 8, the amount of leptin secretion of the Orlistat group, CLA group and N-CLA group decreased by 11.6%, 8.3% and 7.8%, respectively, compared with the control group.

(7) Statistics

The above results were calculated with an SPSS package program (SPSS 12.0 for Windows, USA). The significance to average difference between the control group and test groups was tested with Student's t-test. The significance level was $p<0.05$. All measurement values are represented as mean±S.E.

EXPERIMENTAL EXAMPLE 3-2

Figure 13:
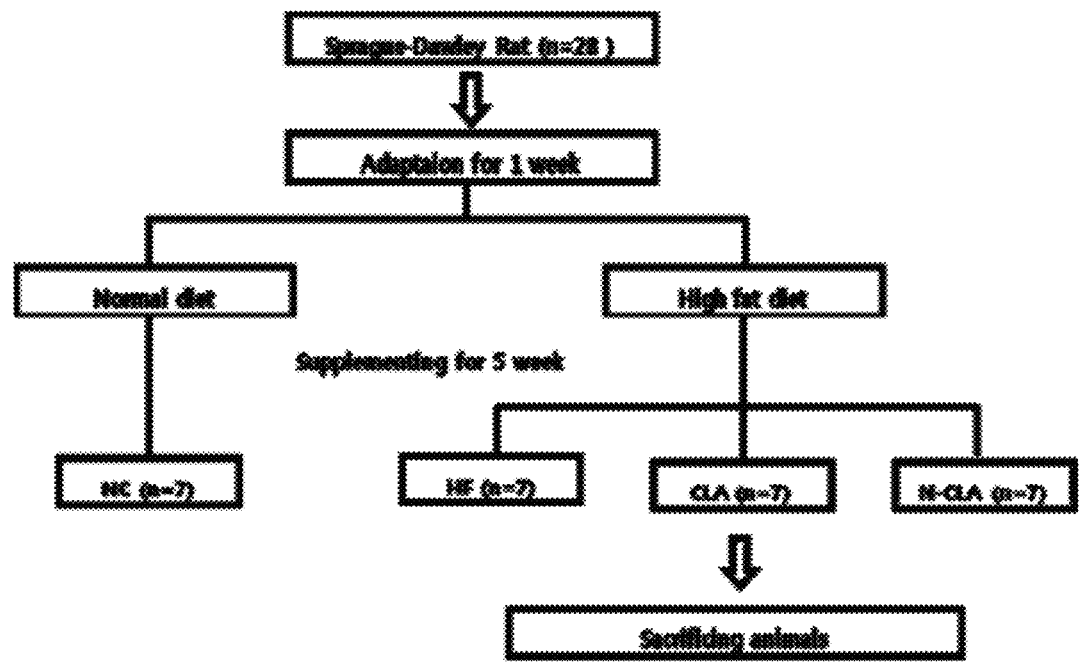
FIG. 13 is a protocol of in vivo study for N-CLA

In Vivo Experiments (1) Experimental Animal and Experiment Design 28 male Sprague-Dawley rats (5 weeks, 145±5 g) were purchased from the Orient Company (Korea) as experimental animals. Rats were adapted with a lab-chow diet in pellet form for a week. Other obesity-induction groups except the normal group (NC) were fed high fat diet ad libitum for 5 weeks to induce obesity, and then rats were divided into four groups (7 rats per group) including the normal group and bred for 5 weeks as represented in FIG. 13.

AIN-76 diet (Teklad, USA) was used as a base of the experimental diet. Test materials were added at the level of 2% of high fat diet. The composition of the experimental diets is shown in Table 15. In the CLA group and N-CLA group, 2% of CLA and N-CLA were added, respectively, while reducing corn oil. Experimental diet and water were supplied ad libitum. During the breeding period, the experimental diets were kept in a 4° C. refrigerator. Each of the animals was placed in an empty cage under a specific environmental condition, at 25±2° C. with a relative humidity of 60±5%, a lighting cycle of 12 hr light/12 hr dark. Body weight and the amount of diet intake were measured at constant time at 2-day intervals during the overall experimental period. Feed efficiency ratio (FER) was calculated by dividing the amount of body weight gain during the experimental period with the amount of diet intake during the same period, and the results are represented in Table 16.

TABLE 15

Composition of the experimental diets

| Ingredients | ND (Normal diet) | HFD (High-fat diet) | CLA (HFD + CLA) | (g/kg diet) N-CLA (HFD + N-CLA) |
|---|---|---|---|---|
| Corn starch | 150 | 100 | 100 | 100 |
| Sucrose | 500 | 398.75 | 398.75 | 398.75 |
| Casein | 200 | 200 | 200 | 200 |
| Corn oil | 50 | 50 | 30 | 30 |
| Lard | — | 150 | 150 | 150 |
| Cholesterol | — | 1 | 1 | 1 |
| Sodium chlorate | — | 0.25 | 0.25 | 0.25 |
| Cellulose | 50 | 50 | 50 | 50 |
| AIN-mineral mixture[1] | 35 | 35 | 35 | 35 |
| AIN-vitamin mixture[2] | 10 | 10 | 10 | 10 |
| DL-methionine | 3 | 3 | 3 | 3 |
| Choline bitatrate | 2 | 2 | 2 | 2 |
| CLA | — | — | 20 | — |
| N-CLA | — | — | — | 20 |
| Total | 1000 | 1000 | 1000 | 1000 |

[1]AIN mineral mixture (g/kg): calcium lactate 620.0, sodium chloride 74.0, potassium phosphate di-basic 220.0, potassium sulfate 52.0, magnesium oxide 23.0, manganous carbonate 3.3, ferric citrate 6.0, cupric carbonate 0.2, potassium iodate 0.1, sodium selenite 0.01, chromium potassium sulfate 0.5, finely powdered to make 1,000 g.
[2]AIN vitamin mixture (mg/kg): thiamin-HCl 600, riboflavin ±600, pyridoxine-HCl 700, nicotinic acid 3,000, D-calcium pantothenate 1,600, folic acid 200, D-biotin 20, vitamin B12 2.5, vitamin A 400,000 IU, vitamin D3 100,000 IU, vitamin E 7,500 IU, vitamin K 75, finely powdered to make 1,000 g.

TABLE 16

Comparison of body weight gain, food intake and food efficiency ratio in rats fed experimental diet for 5 weeks

| Group | Food Intake (g/day) | Body Weight Gain (g/day) | FER[1] |
|---|---|---|---|
| ND | 28.46 ± 1.23 | 2.40 ± 0.58 | 0.08 ± 0.02 |
| HFD | 27.50 ± 0.86 | 2.89 ± 0.55 | 0.10 ± 0.02 |
| CLA | 28.18 ± 0.21 | 2.89 ± 0.55 | 0.11 ± 0.02 |
| N-CLA | 28.49 ± 0.71 | 1.37 ± 0.31 | 0.05 ± 0.01 |

ND: normal diet, HFD: high fat diet (HF diet), CLA: HF diet + 2% CLA, N-CLA: HF diet + 2% N-CLA,
[1]FER (food efficiency ratio) = body weight gain/food intake As can be seen in Table 16, the amount of diet intake did not show statistical significance in all groups, and thus it is thought that the amount of diet intake did not affect body weight gain or loss. Meanwhile, body weight gain in the N-CLA group was lower than in the ND group, HFD group and CLA group with statistical significance. Therefore, it can be known that supplement of N-CLA remarkably suppressed body weight gain while not affecting diet intake.

Figure 9:
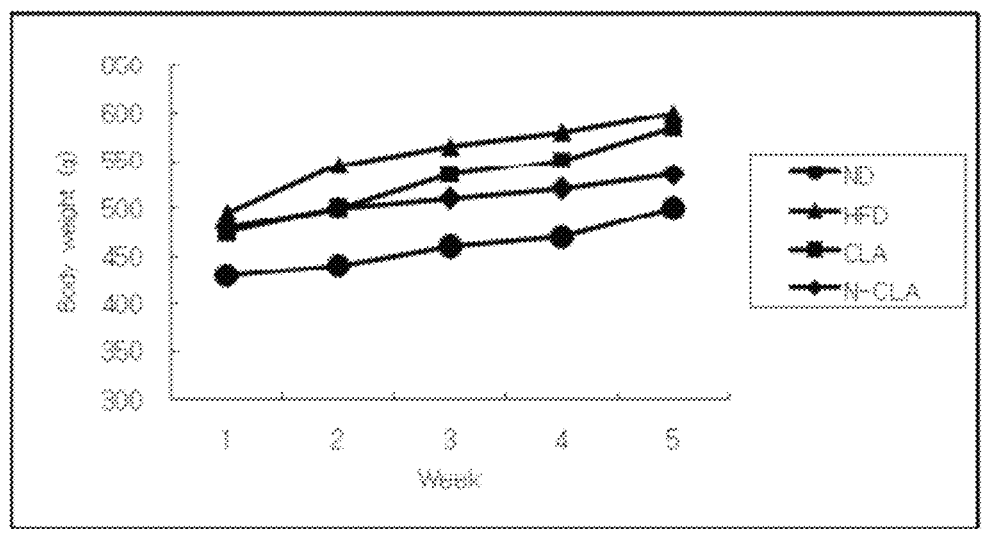
FIG. 9 is a graph representing the result of body weight change during 5 weeks of experiments (ND: normal diet, HFD: high fat diet (HF diet), CLA: HF diet+2% CLA, N-CLA: HF diet+2% N-CLA).

The amount of body weight change during the experiment period is represented in FIG. 9. As can be seen in FIG. 9, body weight of all groups steadily increased during the experiment period. Other groups except the normal diet (ND) group were induced to obesity with a high fat diet for 5 weeks. Body weight measured in the 1$^{st}$ week after obesity induction of all high fat diet intake groups was heavier than in the normal control group with statistical significance. During the 5-week experiment period, the HFD group showed the highest body weight gain. The body weight gain of the CLA group was lower than in the HFD group from the 2$^{nd}$ week to the 4$^{th}$ week, but the body weight of the CLA group in the 5$^{th}$ week was not different from that of the HFD group with statistical significance. Meanwhile, the body weight of the N-CLA group was lighter than in the HFD group from the 2$^{nd}$ week with statistical significance. Specifically, the body weight of the N-CLA group in the 5$^{th}$ week was similar to that of the normal diet (ND) group which was not fed high fat diet. Accordingly, it can be known that supplement of N-CLA efficiently suppressed body weight gain.

(2) Organ Weight

Figure 10:
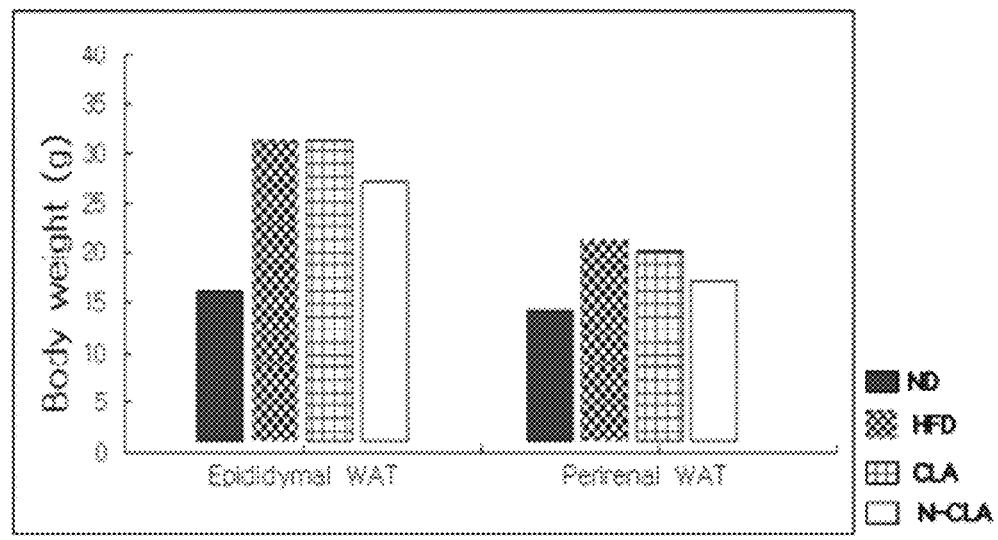
FIG. 10 is a graph representing the measurement result of weight per unit body weight of epididymal white adipose tissue and perirenal white adipose tissue (ND: normal diet, HFD: high fat diet (HF diet), CLA: HF diet+2% CLA, N-CLA: HF diet+2% N-CLA; WAT: white adipose tissue; B.W.: body weight).

After breeding, rats were fasted for 12 hours and then primarily anesthetized with ether. Fasting blood was collected from the inferior vena cava. Collected blood was centrifuged at 3,000×g, 4° C. for 15 minutes to obtain serum, and then obtained serum was stored at −70° C. until sample analysis. Organ tissues (liver, heart, kidney, epididymal white adipose tissue and perirenal white adipose tissue) of the experimental animals were washed with PBS (phosphate buffered saline) several times, and then weighed after removing surface moisture. Liver was isolated, collected, rapidly frozen in liquid nitrogen and stored at −70° C. until sample analysis for measurement of enzyme activity and lipid quantification. The results of measuring the weight of liver, heart and kidney are represented in Table 17. The results of measuring the weight of epididymal white adipose tissue and perirenal white adipose tissue per unit body weight are represented in FIG. 10.

TABLE 17

Effect of supplementation of the N-CLA on organ weight in rats fed experimental diet for 5 weeks

| Group | Organ Weight (mg/g B.W.) | | |
|---|---|---|---|
| | Heart | Liver | Kidney |
| ND | 2.91 ± 0.11 | 25.67 ± 0.26 | 6.04 ± 0.41 |
| HFD | 2.51 ± 0.21 | 43.51 ± 0.30 | 5.92 ± 0.49 |
| CLA | 2.43 ± 0.17 | 44.69 ± 2.57 | 5.35 ± 0.24 |
| N-CLA | 2.47 ± 0.20 | 44.28 ± 4.49 | 5.37 ± 0.52 |

ND: normal diet, HFD: high fat diet (HF diet), CLA: HF diet + 2% CLA, N-CLA: HF diet + 2% N-CLA, B.W.: Body weight As can be seen in Table 17, the weight of heart was decreased in all high fat diet intake groups except the normal control group, and the weight of liver was increased in all high fat diet intake groups with statistical significance.

In addition, as can be seen in FIG. 10, as a result of measuring the weight of epididymal white adipose tissue and perirenal white adipose tissue per unit body weight, WAT (white adipose tissue) was increased in all high fat diet intake groups. The weight of epididymal white adipose tissue and perirenal white adipose tissue in the CLA group and N-CLA group was slightly lighter than in the HFD group without statistical significance.

(3) Biochemical Analysis

1) Total-Cholesterol

Quantification of total serum cholesterol was performed by using a test solution (Asanpharm Co., Korea) utilizing Allain et al. (1974)'s enzyme method. Serum cholesterol exists in two forms of CE (cholesterol ester) and free cholesterol. Thus, to quantify both CE and free cholesterol, CE was converted into fatty acid and free cholesterol by cholesterol esterase. Such converted free cholesterol was in turn converted into $H_2O_2$ and $\Delta^4$-cholestenon by cholesterol esterase. $H_2O_2$ was mixed with peroxidase, phenol and 4-amino-antipyrine to emit red color, and then absorbance at 500 nm was measured. The measured values were compared with cholesterol standard solution (300 mg/dL) for the quantification.

2) Triglyceride

Serum neutral lipids were measured by using a reagent for measuring neutral lipid (Asanpharm Co., Korea) according to McGowan et al. (1983)'s enzyme method. Neutral lipids in serum were degraded to glycerol and fatty acid by lipoprotein lipase (LPL). Glycerol formed L-α-glycerophosphate by the action of ATP and glycerol kinase (GK). The reaction of L-α-glycerophosphate with $O_2$ and glycerophosphooxidase (GPO) generated $H_2O_2$. Peroxidase and 4-amino-antipyrine were added thereto to emit red color, and then absorbance at 550 nm was measured. The measured values were compared with glycerol standard curve for the quantification.

3) HDL-Cholesterol, LDL-Cholesterol

The content of HDL-cholesterol was measured with kit reagent (Asanpharm Co., Korea). The content of LDL-cholesterol was calculated according to Friedewald et al. (1993)'s method as follows: LDL-cholesterol=Total cholesterol−HDL-cholesterol−(neutral lipid/5).

Figure 11:
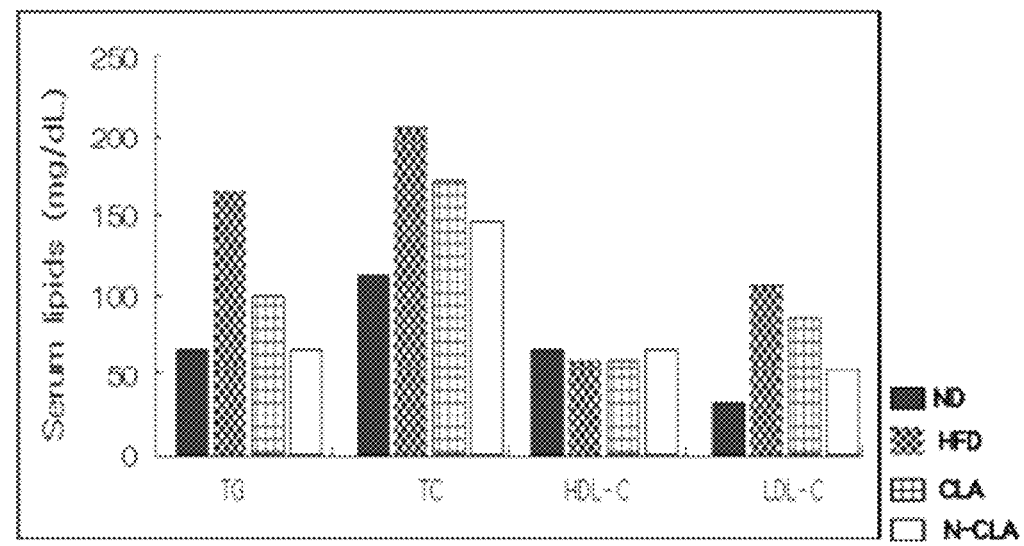
FIG. 11 is a graph representing the measurement result of the content of serum cholesterol and neutral lipid (ND: normal diet, HFD: high fat diet (HF diet), CLA: HF diet+2% CLA, N-CLA: HF diet+2% N-CLA; TG: triglyceride, TC: total cholesterol, HDL-C: high-density lipid cholesterol, LDL-C: low-density lipid cholesterol).

The content of serum neutral lipids and cholesterol measured according to the above method is represented in FIG. 11. As can be seen in FIG. 11, the content of neutral lipid of the HFD group was 2 times or higher than that of the normal diet (ND) group. The content of neutral lipid of the CLA group and N-CLA group was lower than HFD group with statistical significance. Specifically, the content of serum neutral lipid (triglyceride, TG) was fairly close to the level of the normal diet (ND) group. It was decreased by 52% compared with the HFD group. Total cholesterol (TC) and low density lipid (LDL) of the HFD group were far higher than those of the normal diet (ND) group. Total cholesterol (TC) and low-density lipid (LDL) of the CLA group and N-CLA group were decreased compared with the HFD group with statistical significance. Specifically, total cholesterol (TC) and low density lipid (LDL) of the N-CLA group were decreased in 20% and 46%, respectively, compared with the HFD group. Thus, it can be known that N-CLA has an excellent effect on reducing cholesterol. Meanwhile, the concentration of high-density lipid did not show any statistically significant difference in all groups.

4) Liver Tissue Lipid Content

Measurement of lipid content in liver tissue was carried out according to Folch et al.'s method. CM solution (chloroform:methanol=2:1) was added to 1 g of liver tissue and then homogenized. The solution was stored at 4° C. for 3 days with shaking every 12 hours. After 3 days, CM solution layer, which was separated from water layer, was isolated with a pipette, and then dry lipids were obtained by evaporating CM solution entirely in 80° C. water bath. Obtained dry lipids were dissolved in anhydrous ethanol to homogenize, and then the content of neutral lipids, total cholesterol and HDL-cholesterol was measured with a kit reagent (AM 157S-K, AM 202-K, AM 203-K, Asanpharm Co., Korea). The results are represented in FIG. 12.

Figure 12:
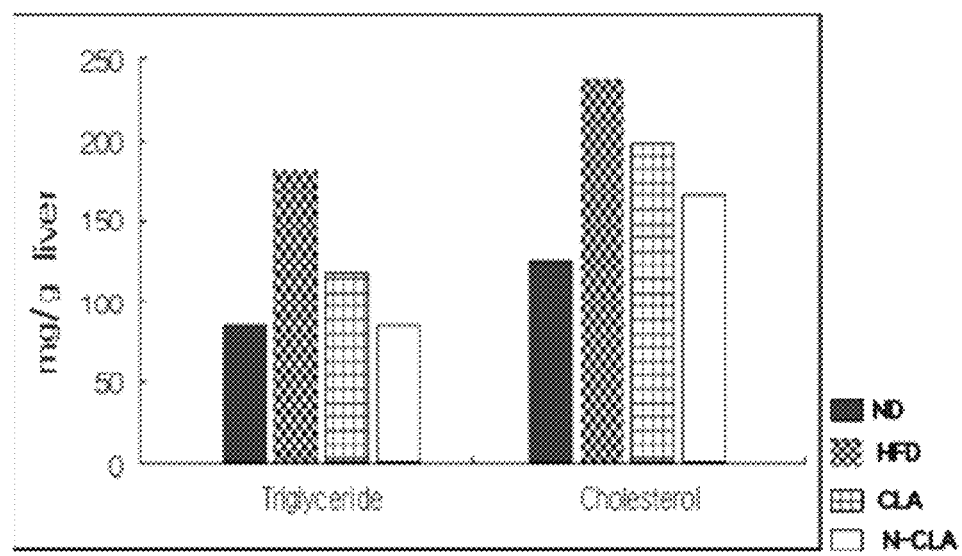
FIG. 12 is a graph representing the measurement result of the content of cholesterol and neutral lipid per gram (g) of liver tissue (ND: normal diet, HFD: high fat diet (HF diet), CLA: HF diet+2% CLA, N-CLA: HF diet+2% N-CLA).

As can be seen in FIG. 12, the content of neutral lipids, total cholesterol in liver tissue of the HFD group was the highest, and the CLA group and N-CLA group showed a statistically significant decrease compared with the HFD group. As with serum lipid level, it can be known that N-CLA reduced the content of liver tissue lipid more efficiently than did CLA.

5) Statistics

The above results were calculated with an SPSS package program. The significance to average difference between each of the groups was tested with one-way ANOVA (analysis of variance). With respect to difference between multiple groups, Post-hoc comparison was performed by Duncan's multiple range test at the level of $p<0.05$. The results are represented as mean±S.E.

The invention claimed is:

1. An aqueous nanoemulsion composition comprising 15 to 50 wt % of conjugated linoleic acid, 0.01 to 5 wt % of lecithin, 0.01 to 5 wt % of ethanol as a dissolution aid, 1 to 15 wt % of coemulsifier, 15 to 35 wt % of glycerine and the balance of water.

2. The composition according to claim 1, wherein viscosity is 1 to 100 centipoise (cP).

3. The composition according to claim 1, wherein said coemulsifier is one or more selected from the group consisting of Polysorbate 20, Polysorbate 80, anionic amino acid-based emulsifier, sugar esters, cholesterol, sodium lauryl sulfate, sodium stearoyl lactylate and glycerine ester.

4. The composition according to claim 3, wherein said anionic amino acid based emulsifier is one or more selected from the group consisting of TEA-cocoyl glutamate, sodium glutamate, sodium cocoyl glutamate, magnesium cocoyl glutamate and sodium lauroyl glutamate.

\* \* \* \* \*